US012312517B2

(12) United States Patent
Zhang et al.

(10) Patent No.: US 12,312,517 B2
(45) Date of Patent: May 27, 2025

(54) ADHESIVE COMPOSITIONS

(71) Applicant: Solventum Intellectual Properties Company, Maplewood, MN (US)

(72) Inventors: Ying Zhang, Woodbury, MN (US); Robert A. Asmus, Hudson, WI (US); Zhicheng Tian, Woodbury, MN (US); Kheng Vang, St. Paul, MN (US); James Dizio, St. Paul, MN (US); Patrick J. Parks, St. Paul, MN (US); Brian E. Spiewak, Inver Grove Heights, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 784 days.

(21) Appl. No.: 17/612,375

(22) PCT Filed: May 18, 2020

(86) PCT No.: PCT/IB2020/054704

§ 371 (c)(1),
(2) Date: Nov. 18, 2021

(87) PCT Pub. No.: WO2020/240337

PCT Pub. Date: Dec. 3, 2020

(65) Prior Publication Data

US 2022/0298389 A1 Sep. 22, 2022

Related U.S. Application Data

(60) Provisional application No. 62/852,730, filed on May 24, 2019.

(51) Int. Cl.

| | |
|---|---|
| ***C09J 7/38*** | (2018.01) |
| ***A61L 15/58*** | (2006.01) |
| ***A61L 24/04*** | (2006.01) |
| ***A61L 31/04*** | (2006.01) |

(52) U.S. Cl.
CPC ............ *C09J 7/385* (2018.01); *A61L 15/585* (2013.01); *A61L 24/043* (2013.01); *A61L 31/04* (2013.01)

(58) Field of Classification Search
CPC . C09J 7/385; C09J 11/06; C09J 133/26; C09J 2333/00; A61L 15/585; A61L 24/043; A61L 31/04
See application file for complete search history.

(56) References Cited

U.S. PATENT DOCUMENTS

| | | | | |
|---|---|---|---|---|
| 3,645,835 | A | 2/1972 | Hodgson | |
| 4,595,001 | A | 6/1986 | Potter | |
| 2010/0282409 | A1* | 11/2010 | Hobbs | A01N 25/02 514/642 |
| 2013/0231394 | A1 | 9/2013 | Arndt | |
| 2015/0328360 | A1* | 11/2015 | Menon | A61L 15/58 514/635 |
| 2019/0366067 | A1* | 12/2019 | Ginggen | A61B 17/32053 |

FOREIGN PATENT DOCUMENTS

| | | | |
|---|---|---|---|
| EP | 0 375 827 | A2 | 7/1990 |
| EP | 3150234 | | 4/2017 |
| JP | 11-349418 | A | 12/1999 |
| WO | WO 2009-088894 | | 7/2009 |
| WO | WO 2014/035981 | A1 | 3/2014 |

OTHER PUBLICATIONS

Dettenkofer, Skin Disinfection with Octenidine Hydrochloride for Central Venous Catheter Site Care: A Double-Blind Randomized, Controlled Trial, Clin Microbiol Infect 2010, vol. 16, pp. 600-606.
Loveday, "epic3: National Evidence-Based Guidelines for Preventing Healthcare-Associated Infections in NHS Hospitals in England", Journal of Hospital Infections 86S1, 2014, pp. S1-S70.
Silvestri, "Chlorhexidine: Uses and Adverse Reactions", Dermatitis, 2013, vol. 24, No. 3, pp. 112-118.
International Search Report for PCT International Application No. PCT/IB2020/054704, mailed on Aug. 24, 2020, 4 pages.

* cited by examiner

*Primary Examiner* — Scott R. Walshon

(57) ABSTRACT

Adhesive compositions are disclosed that include an octenidine salt, a resin system, a plasticizer, and a cidatrope. The dried adhesive compositions are substantially free of water and $C_2$-$C_5$ alcohols. The adhesive compositions disclosed are formulations that provide rapid and persistent antimicrobial activity and may be useful, for example, in wound dressings, surgical drapes, and medical tapes.

17 Claims, No Drawings

ADHESIVE COMPOSITIONS

CROSS REFERENCE TO RELATED APPLICATIONS

This application is a national stage filing under 35 U.S.C. 371 of PCT/IB2020/054704, filed May 18, 2020, which claims the benefit of U.S. Prov. Pat. App. No. 62/852,730, filed May 24, 2019 the disclosures of each of which are incorporated by reference herein in its entirety.

TECHNICAL FIELD

The present disclosure relates to adhesive compositions containing an octenidine salt, a resin system, a plasticizer, and a cidatrope, where the compositions are substantially free of water and $C_2$-$C_5$ alcohols. Also disclosed are articles incorporating such adhesive compositions.

BACKGROUND

It is standard practice in the industrialized world to apply an antiseptic preparation to the skin prior to any invasive procedure such as, for example, surgery, catheterization, or needle puncture, to reduce the risk of infection. Chlorohexidine gluconate ("CHG") is well established in the marketplace for use as a disinfectant and antiseptic for skin disinfection before surgery, but CHG is also used for sterilizing surgical instruments and for cleaning wounds. CHG is increasingly being used not only as an antiseptic to prevent hospital infections and an adjuvant in oral hygiene, but also as a preservative in personal care products. For example, CHG antimicrobial dressings, CHG skin preparations, CHG bathing formulations, and CHG nasal spray.

As exposure to CHG becomes more widespread, reports of adverse reactions to it are increasing. The Food and Drug Administration has warned that serious allergic reactions have been reported with skin antiseptics containing CHG. While reports of these reactions are currently rare, the number of serious allergic reactions to CHG has risen over the last several years.

SUMMARY

Provided herein are adhesive compositions comprising 40 wt. % to 90 wt. % resin system; 0 wt. % to 59.49 wt. % plasticizer; 0.01 wt. % to 10 wt. % octenidine salt; and 0.5 wt. % to 59.99 wt. % cidatrope, where the compositions are substantially free of water and a $C_2$-$C_5$ alcohol.

Features and advantages of the present disclosure will be further understood upon consideration of the detailed description as well as the appended claims.

Definitions

As used herein, the term "ambient temperature" refers to the temperature range between about 21 and 25° C.

As used herein, the term "cidatrope" refers to a component in an antimicrobial composition that enhances the effectiveness of the antimicrobial composition such that when the antimicrobial composition less the antimicrobial agent and the composition less the cidatrope component are used separately, they do not provide the same level of antimicrobial activity as the antimicrobial composition including both the antimicrobial agent and the cidatrope. For example, a cidatrope component in the absence of the antimicrobial agent does not provide any appreciable antimicrobial activity. The enhancing effect can be with respect to the level of kill, the speed of kill, and/or the spectrum of microorganisms killed, and may not be seen for all microorganisms. The cidatrope component may be a synergist such that when combined with the remainder of the composition, the composition as a whole displays an activity that is greater than the sum of the activity of the composition less the cidatrope component and the composition less the antimicrobial agent. The cidatrope may be a solid or liquid at ambient temperature conditions As used herein, the term "dried composition" refers to a composition subjected to a process, e.g., heating, vacuum drying, whereby any volatile component that might be introduced to the composition during preparation has been removed such that the composition is substantially free of the volatile component.

As used herein, the term "nonvolatile" refers to a component that does not evaporate readily at ambient temperature conditions, such that a 20 g sample in a 4 $cm^2$ dish does not lose more than 2% of its weight within 60 minutes upon exposure to ambient temperature conditions. Examples of nonvolatile components of the compositions described herein include the disclosed octenidine salts, resin systems, plasticizers, and cidatropes.

As used herein, the term "solvent" refers to any organic compound used to dissolve or disperse another compound.

As used herein, the term "surfactant" is synonymous with "emulsifier," and means an amphiphile (i.e., a molecule possessing both polar and nonpolar regions which are covalently bound) capable of reducing the surface tension of water and/or the interfacial tension between water and an immiscible liquid.

As used herein, the term "substantially free" means less than 1% by weight, less than 0.5% by weight, or less than 0.1% by weight, of a component based on the total weight of the composition.

As used herein the phrase "substantially free of water and a $C_2$-$C_5$ alcohol" refers to a composition free of water and a $C_2$-$C_5$ alcohol or a composition having less than 1% by weight, less than 0.5% by weight, or less than 0.1% by weight water and a $C_2$-$C_5$ alcohol, based on the total weight of the dried composition.

As used herein, the term "volatile" refers to a component that evaporates readily at ambient temperature conditions, such that a 20 g sample in a 4 $cm^2$ dish loses more than 2% of its weight within 60 minutes upon exposure to ambient temperature conditions. Examples of volatile components described herein include water and $C_2$-$C_5$ alcohols.

DETAILED DESCRIPTION

Octenidine salts are antimicrobial agents that destroy or otherwise hinder the growth and reproduction of pathogenic microbes. Octenidine salts are intended for use in all mammalian, food-producing species for skin and mucosal disinfection and short-term supportive antiseptic wound treatment. Octenidine salts have been used as an antiseptic agent in human medicine. Resonance structures of one octenidine salt, octenidine dihydrochloride, are shown in Scheme I.

Scheme I

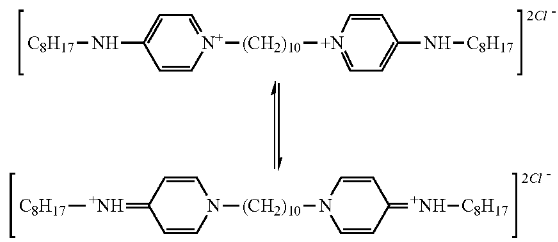

Octenidine salts have been shown to be highly effective against a wide range of microorganisms and display low absorption and toxicity. Studies have demonstrated that octenidine salts in alcoholic solution may be a better option than alcohol alone for the prevention of central venous catheter-associated infections, and may even be as effective as CHG, but without the adverse reactions that may occur when CHG is used with CHG-sensitive patients.

It has been surprisingly discovered that the antimicrobial efficacy of octenidine salts can be improved when used in combination with a cidatrope in adhesive compositions. The adhesive compositions described herein display improved antimicrobial efficacy, which means any one or a combination of the following: (i) the adhesive composition maintains antimicrobial activity despite the presence of a component that is known to affect an octenidine salt; (ii) the adhesive composition demonstrates improved antimicrobial activity relative to the same adhesive composition without one of either the plasticizer or the cidatrope present; or (iii) the adhesive composition with less octenidine salt present maintains the same activity relative to an adhesive composition with more octenidine salt present but lacking one of either the plasticizer or the cidatrope; or (iv) the composition shows synergistic antimicrobial activity when the octenidine salt, plasticizer, and cidatrope are present.

Provided herein are adhesive compositions including an octenidine salt, a resin system, a plasticizer, and a cidatrope, where the dried adhesive compositions are substantially free of water and $C_2$-$C_5$ alcohols. The adhesive compositions disclosed herein are formulations that provide rapid and persistent antimicrobial activity and may be useful, for example, in wound dressings or surgical drapes for attaching the wound dressing or surgical drape to a patient's skin while also reducing the likelihood that infectious microbes will be introduced through a wound covered by the wound dressing or surgical drape. The adhesive compositions disclosed herein may also be useful in medical tapes.

The disclosed adhesive compositions have rapid bactericidal activity due to the enhanced activity of the antimicrobial agent in the presence of the cidatrope. Such enhanced activity may allow for the use of lower concentrations of antimicrobial agents than would otherwise be possible, thus allowing for production of formulations having reduced risk of issues that may arise when higher concentrations of antimicrobial agents are used on human skin, such as, for example, skin sensitivity and/or irritation. Other benefits of the disclosed adhesive compositions including lower concentrations of antimicrobial agents than would otherwise be possible due to the enhanced activity of the antimicrobial agent in the presence of the cidatrope can include, for example, lower costs for production of the adhesive compositions and improved environmental impact (e.g., less antimicrobial agent ending up in waste-treatment facilities). The use of lower doses of antiseptic can carry an additional benefit of reducing or removing the possibility of antiseptic 'resistance' developing, where 'resistance' implies the requirement to use a higher amount of antimicrobial agent to achieve the same rate of microbial control. The disclosed adhesive compositions can provide persistent bactericidal activity on the skin and may be non-irritating, particularly as they do not include chemical substances that can be skin irritants, such as, for example, $C_2$-$C_5$ alcohols or surfactants.

Octenidine Salts

Octenidine salts useful in embodiments of the present disclosure include octenidine salts such as, for example, octenidine dihydrochloride, octenidine gluconate, octenidine sulfate, octenidine acetate, and combinations thereof. Octenidine dihydrochloride is commercially available from TCI America, Portland, OR, USA.

Suitable concentrations of the octenidine salts in adhesive compositions of the present disclosure include concentrations that are high enough to effectively reduce microbial contamination and low enough such that the octenidine salts remains solubilized in the adhesive composition. Examples of suitable octenidine salts concentrations in adhesive compositions of the present disclosure generally range from about 0.01 wt. % to about 30% by weight. The suitable concentrations may vary depending on factors such as, for example, the composition of the resin system, the identity of the plasticizer and/or the cidatrope, and the desired level of antimicrobial activity.

In some embodiments, the octenidine salt is at least 0.01 wt. %, at least 0.025 wt. %, at least 0.05 wt. %, at least 0.1 wt. %, at least 0.25 wt. %, at least 0.5 wt. %, at least 1 wt. %, or at least 1.5 wt. % based on the total weight of nonvolatile components in the composition. In some embodiments the octenidine salt is no more than 10 wt. %, no more than 9 wt. %, no more than 8 wt. %, no more than 7 wt. %, no more than 6 wt. %, no more than 5 wt. %, no more than 4 wt. %, or no more than 3 wt. % based on the total weight of nonvolatile components in the composition. In some embodiments the octenidine salt is commonly 0.01 wt. % to 10 wt. %, 0.025 wt. % to 9 wt. %, 0.05 wt. % to 8 wt. %, 0.1 wt. % to 7 wt. %, 0.25 wt. % to 6 wt. %, 0.5 wt. % to 5 wt. %, 1 wt. % to 4 wt. %, or 1.5 wt. % to 3 wt. %, based on the total weight of nonvolatile components in the composition.

Cidatrope

Cidatropes suitable for use in compositions of the present disclosure include $C_8$-$C_{26}$ alcohols, ethers, amides, esters, and combinations thereof. In some embodiments, the $C_8$-$C_{26}$ alcohol cidatrope is selected from the group consisting of 1-tetradecanol, hexadecanol, 16-methyl-1-heptadecanol, and combinations thereof. In some embodiments, the ether cidatrope is a propoxylated $C_2$ to $C_{18}$ alcohol having a degree of propoxylation of 2 to 50 moles per mole of alcohol. In some embodiments, the amide cidatrope is selected from the group consisting of a coconut fatty acid monoethanol amide, a coconut fatty acid methyl ethanolamide, an alkyl alkanolamide, and combinations thereof. In some embodiments, the ester cidatrope is selected from the group consisting of diisopropyl adipate, dibutyl sebacate, triethyl citrate, tributyl citrate, acetyltributyl citrate, octyldodecyl neopentanoate, laureth-2-acetate, isopropyl myristate, trioctyldodecyl citrate, myristyl myristate, cetyl acetate, and combinations thereof.

In some embodiments, the cidatrope is at least 0.5 wt. %, at least 0.75 wt. %, at least 1 wt. %, at least 1.25 wt. %, or at least 1.5 wt. % of the adhesive composition based on the total weight of nonvolatile components in the composition.

In some embodiments, the cidatrope is no more than 59.99 wt. %, no more than 40 wt. %, no more than 20 wt. % no more than 10 wt. %, or no more than 5 wt. % of the adhesive composition based on the total weight of nonvolatile components in the composition. In some embodiments the cidatrope is 0.5 wt. % to 59.99 wt. %, 0.75 wt. % to 40 wt. %, 1 wt. % to 20 wt. %, 1.25 wt. % to 10 wt. %, or 1.5 wt. % to 5 wt. % of the adhesive composition based on the total weight of nonvolatile components in the adhesive composition.

In some embodiments, the cidatrope may also function as a plasticizer in adhesive compositions of the present disclosure, either as the sole plasticizer in the adhesive composition or as a plasticizer used in combination with another plasticizer as disclosed below. In such embodiments, the cidatrope also functioning as a plasticizer may be more than 15 wt. %, more than 20 wt. %, more than 30 wt. %, more than 40 wt. %, or more than 50 wt. % of the adhesive composition based on the total weight of nonvolatile components in the adhesive composition. In such embodiments, the cidatrope also functioning as a plasticizer may be less than 59.99 wt. %, less than 58 wt. %, or less than 55 wt. % of the adhesive composition based on the total weight of nonvolatile components in the adhesive composition. In such embodiments, the cidatrope also functioning as a plasticizer may be 15 wt. % to 59.99 wt. %, 20 wt. % to 59.99 wt. %, 30 wt. % to 59.99 wt. %, 40 wt. % to 58 wt. %, or 50 wt. % to 55 wt. % of the adhesive composition based on the total weight of nonvolatile components in the adhesive composition. In some embodiments, a cidatrope that also functions as a plasticizer may be a substituted citrate, such as, for example, acetyltributyl citrate.

In some embodiments, the weight percentage of cidatrope:octenidine salt in the adhesive composition based on the total weight of nonvolatile components in the adhesive composition is 0.1:1 to 3000:1, such as, for example, 0.1:1, 0.25:1, 0.5:1, 0.75:1, 1:1, 1.25:1, 1.5:1, 2:1, 3:1, 4:1, 5:1, 6:1, 7:1, 8:1, 9:1, or 10:1, 15:1.20:1, 25:1, 30:1, 35:1, 50:1, 100:1, 200:1, 300:1, 400:1, 500:1, 600:1, 700:1, 800:1, 900:1, 1000:1, 2000:1, 3000:1.

Resin System

Resin systems of the present disclosure generally include least one polymer. Suitable polymers may include, for example, polyesters, polyester polyols, polyurethanes, polyalkylenes, acrylates, rubbers, block copolymers, and combinations thereof. In some applications, the resin system may be an adhesive, e.g., a pressure sensitive adhesive ("PSA").

In some embodiments, the PSA comprises an acrylic polymer or copolymer comprising the reaction product of a mixture comprising at least one alkyl (meth)acrylate monomer. As used herein, "(meth)acrylate" refers to an acrylate and/or methacrylate. For example, butyl (meth)acrylate refers to butyl acrylate and/or butyl methacrylate. In some embodiments, the mixture may also include a crosslinking agent.

In some embodiments, the alkyl group of at least one alkyl (meth)acrylate contains 4 to 18 carbon atoms. In some embodiments, this alkyl group contains at least 5 carbon atoms. In some embodiments, this alkyl group contains no greater than 8 carbon atoms. In some embodiments, the alkyl group of the first alkyl (meth)acrylate has eight carbon atoms, e.g., isooctyl (meth)acrylate and/or 2-ethylhexyl (meth)acrylate. In some embodiments, the alkyl group of the first alkyl (meth)acrylate has for carbon atoms, e.g., butyl (meth)acrylate.

In some embodiments, the mixture may comprise one or more additional monomers including one or more additional alkyl(meth)acrylates. In some embodiments, the alkyl group of at least one of the additional alkyl (meth)acrylates contains no greater than 4 carbon atoms. In some embodiments, the alkyl group of at least one alkyl (meth)acrylate has 4 carbon atoms, e.g., butyl (meth)acrylate. In some embodiments, the alkyl group of at least one alkyl (meth)acrylate has 1-2 carbon atoms, e.g., methyl acrylate and/or ethyl acrylate.

Examples of suitable polar monomers that may be copolymerized with the alkyl (meth)acrylate monomers include acidic monomers such as carboxylic acid monomers as well as various acrylamides and hydroxyl alkyl acrylates. Particular examples of polar monomers include vinyl carboxylic acids such as acrylic acid, methacrylic acid, itaconic acid, maleic acid, and fumaric acid and hydroxyl alkyl acrylates and methacrylates, such as 2-hydroxyethyl acrylate or methacrylate. Other suitable polar monomers include N-vinyl pyrrolidone, N-vinyl caprolactam, acrylamide, methacrylamide, N-substituted and N,N-disubstituted acrylamides such as N-ethyl acrylamide, N-hydroxyethyl acrylamide, N,N-dimethyl acrylamide, N,N-diethyl acrylamide, and N-ethyl,N-dihydroxyethyl acrylamide, acrylonitrile, methacrylonitrile and maleic anhydride. Various combinations of such polar monomers can be employed.

Optionally, one or more monoethylenically unsaturated co-monomers may be polymerized with the acrylate or methacrylate monomers. One group of useful co-monomers includes those having a homopolymer glass transition temperature greater than the glass transition temperature of the (meth)acrylate homopolymer. Examples of suitable co-monomers falling within this group include acrylic acid, acrylamides, methacrylamides, substituted acrylamides (such as N,N-dimethyl acrylamide), itaconic acid, methacrylic acid, acrylonitrile, methacrylonitrile, vinyl acetate, N-vinyl pyrrolidone, isobornyl acrylate, cyano ethyl acrylate, N-vinylcaprolactam, maleic anhydride, hydroxyalkyl (meth)-acrylates, N,N-dimethyl aminoethyl (meth)acrylate, N,N-diethylacrylamide, beta-carboxyethyl acrylate, vinyl esters of neodecanoic, neononanoic, neopentanoic, 2-ethylhexanoic, or propionic acids (e.g., those available from Union Carbide Corp. of Danbury, Conn., under the designation VYNATES), vinylidene chloride, styrene, vinyl toluene, and alkyl vinyl ethers.

A second group of monoethylenically unsaturated co-monomers that may be polymerized with the acrylate or methacrylate monomers includes those having a homopolymer glass transition temperature (Tg) less than the glass transition temperature of the (meth)acrylate homopolymer. Examples of suitable co-monomers falling within this class include ethoxyethoxyethyl acrylate (Tg=−71° C.) and a methoxypolyethylene glycol 400 acrylate (Tg=−65 71° C.; available from Shin Nakamura Chemical Co., Ltd. Japan, under the designation "NK Ester AM-90G").

In some embodiments, the PSA comprises a block copolymer. In some embodiments, the block copolymer is a styrenic block copolymer, i.e., a block copolymer comprising at least one styrene hard segment, and at least one elastomeric soft segment. Exemplary styrenic block copolymers include dimmers such as styrene-butadiene ("SB") and styrene-isoprene ("SI"). Additional exemplary styrenic block copolymers include styrene-isoprene-styrene ("SIS"), styrene-butadiene-styrene ("SBS"), styrene-ethylene/butadiene-styrene ("SEBS"), and styrene-ethylene/propylene-styrene block copolymers. In some embodiments, radial and star block copolymers may be used. Commercially available styrenic block copolymers include those available under the trade designation KRATON from Kraton Polymers LLC. including, e.g., KRATON D SBS and SIS block copolymers; and KRATON G SEBS and SEPS copolymers. Additional commercially available di- and tri-block styrenic block copolymers include those available under the trade designations SEPTON and HYBAR from Kuraray Co. Ltd., those available under the trade designation FINAPRENE from Total Petrochemicals, and those available under the trade designation VECTOR from Dexco Polymers LP.

The resin systems of the present disclosure may contain any of a variety of known additives including, e.g., crosslinkers, photoinitiators, curing agents, tackifiers, fillers, colorants, e.g., dyes, pigments, waxes antioxidants and the like. As used herein, the terms tackifier is used relative to the material or phase into which it is incorporated. Thus, a "tackifier" is a material that is compatible with and raises the glass transition temperature of a material.

In some embodiments, adhesive compositions of the present disclosure include resin systems where the polymer comprises 70 wt. % to 95% wt. % of a first monomer, where the first monomer is a low Tg acrylate monomer selected from the group consisting of iso-octyl acrylate, 2-ethyl hexyl acrylate, 2-octyl acrylate, and butyl acrylate; 1 wt. % to 25 wt. % of a second monomer, where the second monomer is a polar, non-acidic monomer selected from the group consisting of acrylamide, N-vinyl pyrrolidone, and hydroxyl alkyl acrylate; and 0 wt. % to 20 wt. % vinyl acetate or butyl vinyl ether. In some embodiments, the first monomer comprises iso-octyl acrylate and the second monomer comprises acrylamide. In some embodiments the polymer comprises vinyl acetate or butyl vinyl ether. In some embodiments, the resin system resin system has a modulus of 50,000 to 1,000,000 Pa at 25° C. In some embodiments the resin system is a pressure sensitive adhesive. In some embodiments, the modulus of the pressure sensitive adhesive is 10,000 to 200,000 Pa at 25° C.

Plasticizer

Plasticizers useful in adhesive compositions of the present disclosure are compatible with the resin systems described above. In disclosed adhesive compositions the plasticizer functions as a solvent for the octenidine salt and the cidatrope and may function to reduce the glass transition temperature ("Tg") of the resin system. Preferably, the plasticizer is non-toxic and non-irritating to human skin.

Plasticizers suitable for use in compositions of the present disclosure include glycols (compounds having at least two hydroxyl groups per molecule) such as PEGs having a molecular weight below 2000 and preferably less than 1000 and most preferably less than about 800 daltons; glycerin and polyglycerols, propylene glycol, dipropylene glycol, tripropylene glycol, polypropylene glycol, ethylene oxide/propylene oxide random or block copolymers, ethoxylated polyhydric alcohols, trimethylolpropane, pentracrithiritol, sorbitol, panetothenol, glucuronolactone, gluconic acid, and the like as well as other polar solvents such as N-methylpyrrolidone, propylene carbonate, butyrolactone, and the like.

In some embodiments, the plasticizer may include glyceryl monoisostearate, glyceryl monooleate, decagylcerol hexaoleate, decagylcerol decaoleate, and combinations thereof.

In some embodiments the plasticizer is at least 1 wt. %, at least 2.5 wt. %, at least 5 wt. %, at least 10 wt. %, or at least 15 wt. % of the adhesive composition based on the total weight of the dried composition. In some embodiments the plasticizer is commonly no more than 59.49 wt. %, no more than 50 wt. %, no more than 40 wt. %, no more than 30 wt. %, or no more than 20 wt. %, of the adhesive composition based on the total weight of nonvolatile components in the composition. In some embodiments the plasticizer is 0 wt. % to 59.49 wt. 6, 1 wt. % to 50 wt. %, 2.5 wt. % to 40 wt. %, 5 wt. % to 30 wt. %, or 10 wt. % to 20 wt. % of the adhesive composition based on the total weight of nonvolatile components in the adhesive composition.

Preparation of Adhesive Compositions

Adhesive compositions of the present disclosure may be prepared according to procedures known to those of skill in the relevant arts. For example, a resin system, a plasticizer, an octenidine salt, and a cidatrope, all as described above, may be combined in an appropriate vessel, e.g., a glass jar, and mixed at room temperature, e.g., 23° C., for a time sufficient to produce an adhesive solution, e.g., 6 hours to 24 hours.

Use of Adhesive Compositions

Adhesive compositions of the present disclosure may be bonded to at least a portion of the surface of a substrate, where the substrate is capable of supporting the adhesive layer. In some embodiments, the substrate has a substantially smooth major surface, is flexible, and is optionally conformable. Examples of useful substrates include, for example nonwoven fabrics, polymer films, and metal foils. The substrate may, for example, comprise a web, belt, roll, or sheet. The adhesive composition may cover all or only a portion of the major surface of the substrate, and it may be uniformly coated to form a film substantially free of voids or it may be pattern coated. Pattern coating may be used, for example, to increase moisture vapor transmission.

Useful substrates may include, for example, flexible films and nonwovens. Examples of materials that may be used in the flexible films and nonwovens include polyolefins (e.g., polyethylenes, polypropylenes, polybutylenes, and metallocene polyolefins such as polyolefin elastomers available under the trade designation ENGAGE, and polyolefin plastomers available under the trade designation AFFINITY, from Dow Chemical Co., Midland, Mich.), polyesters (e.g., those available under the trade designation HYTREL from E.I. du Pont de Nemours & Co., Wilmington, Del.), polyamides, styrene/butadiene copolymers (e.g., those available under the trade designation KRATON from Kraton Polymers, Houston Tex.), and polyurethane elastomers (e.g., those polyurethane elastomers available under the trade designations ESTANE 5701, ESTANE 58309, ESTANE 58237, and ESTANE 5702); rayon, chloroprene rubber, ethylene/propylene rubbers, polybutadiene rubber, polyisoprene rubber, natural or synthetic rubber, butyl rubber, silicone rubber, or EPDM rubber; and combinations thereof. In some embodiments, the substrate comprises a high moisture vapor permeable film; for example, as described in U.S. Pat. No. 3,645,835 (Hodgson) and U.S. Pat. No. 4,595,001 (Potter et al.). In some embodiments, the substrate and the adhesive layer may be obtained as a composite article (i.e., with the adhesive layer disposed on the substrate).

In some embodiments the substrate is desirably readily conformable to anatomical surfaces, although this is not a requirement. As such, when applied to an anatomical surface, the substrate may conform to the surface even when the surface is moved, and can stretch and retract. In some embodiments, the backing comprises an elastomeric polyurethane film, polyester film, or polyether block amide film. In some embodiments, the substrate including the adhesive may be part of a medical article, such as, for example, a self-adhesive dressing, a surgical drape, or a medical tape.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

| Material | Source |
|---|---|
| Isooctyl acrylate | 3M Company, Cordova, IL, USA |
| Acrylamide | Zibo Chemical Company, Shandong, China |
| Vinyl acetate | Celanese, Irving, Texas, USA. |
| 2,2'Azobis-(2-methylbutyronitrile) | DuPont, Wilmington, DE, USA |
| Ethyl acetate | Honeywell, Morristown, NJ, USA |
| Methanol | VWR, Radnor, PA, USA |
| 1-Methoxy-2-propanol | Alfa Aesar, Tewksbury, MA, USA |
| Glyceryl monoisostearate | Croda, Edison, NJ, USA |
| Glyceryl monooleate | Croda, Edison, NJ, USA |
| PRISORINE (3515-LQ) | Croda, Edison, NJ, USA |
| ARLAMOL (PC 10-AQ) | Croda, Edison, NJ, USA |
| Diisopropyl adipate | TCI America, Portland, OR, USA |
| Dibutyl sebacate | Spectrum, New Brunswick, NJ, USA |
| Triethyl citrate | Morflex, INC, Greensboro, NC, USA |
| Tributyl citrate | Spectrum, New Brunswick, NJ, USA |
| Myristyl alcohol | Spectrum, New Brunswick, NJ, USA |
| Glycerol | Croda, Edison, NJ, USA |
| Propylene glycol dipelargonate | Henkel Corporation, Dusseldorf, Germany |
| Octyldodecyl neopentanoate | Alzo, Sayreville, NJ, USA |
| Pelemol L2A | Phoenix Chemicals, Branchburg, NJ, USA |
| Isopropyl Myristate | Cognis, North Rhine-Westphalia, Germany |
| Trioctyldodecyl citrate | Alzo, Sayreville, NJ, USA |
| Propylene glycol isostearate | Henkel Corporation, Dusseldorf, Germany |
| Myristyl myristate | Croda, Edison, NJ, USA |
| Cetyl acetate | Phoenix Chemicals, Branchburg, NJ, USA |
| PPG-10-Butanediol | Croda, Edison, NJ, USA |
| Jarcol I-18CG | Jarchem Industries, Newark, NJ, USA |
| Octenidine dihydrochloride | TCI America, Portland, OR, USA |
| PELLETHANE 5863-86A-VG fdm | Lubrizol, Wickliffe, OH, USA |
| Trypticase Soy Agar | Becton Dickinson, Franklin Lakes, NJ, USA |
| DIFCO Neutralizing Buffer | Becton Dickinson, Franklin Lakes, NJ, USA |
| Butterfields Buffer | 3M Company, Maplewood, MN, USA |
| 4-oz. Jar, Cat. #16195-780 | VWR, Radnor, PA, USA |

Testing Methods

All dressings samples consist of: polyurethane film; adhesive with or without octenidine dihydrochloride coating the polyurethane film; and a silicone-coated paper liner covering the adhesive surface.

Moisture Vapor Transmission Rate ("MVTR") Tests

Dressing samples are pre-cut to a disc shape having a diameter of 3.8 cm. The paper liner is removed from the adhesive surface of the dressing and the disc is placed between two foil rings with elliptical openings, thus exposing a dressing sample surface area of 5.1 $cm^2$ and forming a foil/dressing/foil assembly (the "assembly")).

To test upright MVTR, 50 ml of deionized water is placed inside a 4-oz. jar. One or two drops of methylene blue mixture (0.17% wt/wt methylene blue aqueous solution) are added to the jar as a visual aid to detect sample leakage. An assembly is placed on the rubber washer ring over the bottle mouth with the adhesive surface of the assembly facing downward toward the interior of the jar. The jar is placed in a chamber at a temperature of 40° C. 1° C. and 20% relative humidity for four hours. A sealing ring having a circular opening in its center, the opening having a diameter of 1.5 in. (3.8 cm), is tightened onto the jar mouth while the jar is inside the chamber to secure the assembly to the jar. The jar is removed from the chamber and weighed immediately; the mass is recorded as $W_1$. The jar is returned to the chamber for a minimum of eighteen hours (the "test period"), then the jar is removed from the chamber and is immediately reweighed; the mass is recorded as $W_2$. The time the jar is in the chamber after measuring $W_1$, i.e., the test period, is recorded as T. The upright MVTR is calculated using Formula I below:

$$\frac{MVTR = (W1 - W2)4.74 \times 10^4}{T \text{ (hours) minimum } 18} \qquad \text{Formula I}$$

$W1$ = initial weight (grams)

$W2$ = final weight (grams)

$T$ = time (hours)

where:

$W_1$ is the mass of bottle before test period;

$W_2$ is the mass of bottle after test period; and

T is the test period in hours.

For the inverted MVTR measurement, a jar with assembly is prepared as described above, but the jar is placed in a rack such that the mouth of the jar is below the base of the jar and the solution inside the jar is in contact with the assembly during storage. The inverted MVTR measurements are taken as described above for the upright MVTR test. The inverted MVTR calculations are carried out using Formula I. The tests are done in triplicate. The reported results are an average of three measurements.

Adhesion to Steel Test

Dressing samples are cut to dimensions of 2.54 centimeters by 12.7 centimeters. The liner is removed from the dressing sample and the dressing sample is placed, adhesive side down, on a #320 stainless steel test panel. The dressing sample is secured to the test panel using two passes of a 2.0 kg steel roller. The peel test is carried out using a Z005 Tensile Tester (Zwick Roell Group, Kennesaw, Georgia, USA) equipped with a 50 kg load cell at room temperature with a separation rate of 30.5 centimeters/minute. The average peel force is recorded and used to calculate the average peel adhesion strength in gram/centimeter. The tests are done in triplicate. The reported results are an average of three measurements.

Tensile at Break, Ultimate Elongation at Break, and Fn10 Modulus Tests

Tensile strength at break, ultimate elongation at break, and Fn10 modulus measurements are conducted according to a method modified from PSTC-31, ASTM D882, and D3759 test methods and using a Z005 Tensile Tester with clamp-type jaws (Zwick Roell Group, Kennesaw, Georgia, USA) at a constant rate of 25.4 cm/minute.

Dressing samples are cut into 2.54 cm by 2.54 cm squares. One end of the sample square is aligned and clamped to the upper jaw contact line with the dressing length being perpendicular to the upper jaw, then the other end of the sample is gently aligned and clamped to the lower jaw while applying no tension on the sample. The crosshead is then started and the test is continued until the sample ruptures or breaks. The tensile strength at break, ultimate elongation at break and Fn10 modulus are recorded automatically by the instrument. The tests are done in triplicate. The results are an average of three measurements.

Preparation of Base Polymers

Isooctyl acrylate (355 g), acrylamide (45 g), and vinyl acetate (100 g) were added to a 2 L stainless steel Buchi reactor. Ethyl acetate (375 g) and methanol (125 g) were added to the reactor. The reactor was heated up to 55° C. with an agitation speed of 150 rpm. After that, 2,2'azobis-(2-methylbutyronitrile) initiator (0.5 g) was added to the solution. The reaction was started by purging the solution with nitrogen several times to remove all oxygen. The reaction was stirred at 150 rpms at 55° C. for 12 hours and then at 65° C. for 5.25 hours. After the reaction completed, ethyl acetate (442 g) and methanol (225 g) were added to the reactor to dilute the solution.

Base Polymer Analysis:

A mixed standard curve containing isooctyl acrylate and acrylamide is prepared from 1 ppm (w/w) to 1,000 ppm (w/w) for each component in methanol. In order to measure the monomers isooctyl acrylate and acrylamide residual in the base polymer, the base polymer sample was prepared at 25% (w/w) in methanol to form a sample solution. The addition of methanol causes a precipitate to form. The sample solution was mixed on a shaker for approximately 10 minutes until the polymer was completely dissolved in the solvent. The sample solution was then centrifuged at 4500 rpm for five minutes to settle out the solids. The supernatant liquid was then analyzed for isooctyl acrylate and acrylamide residue. The standards and sample were run on an Agilent 1260 HPLC with a diode array detector using an Agilent Zorbax Bonus RP column (3.5 um, 4.6×75 mm) (Agilent Technologies, Santa Clara, California, USA).

Vinyl Acetate Analysis:

A vinyl acetate standard curve was prepared from 1 ppm (w/w) to 2,500 ppm (w/w) in acetonitrile. In order to measure the monomer vinyl acetate residual in the base polymer, the sample was prepared at 5% (w/w) in acetonitrile. A white solid formed while mixing the sample solution, but centrifugation was not necessary to get a clear solution for analysis. The standards and sample were run on an Agilent 7890B GC system with a flame ionization detector using an Agilent HP-1 Column (30 m, 025 mm ID, 1 um df) (Agilent Technologies, Santa Clara, California, USA).

2,2'azobis-(2-methylbutronitrile) Analysis

A 2,2'azobis-(2-methylbutyronitrile) standard curve was prepared from 1 ppm (W/W) to 1,000 ppm (W/W) in methyl tert-butyl ether. In order to measure the monomer 2,2'azobis-(2-methylbutyronitrile) residual in the base polymer, the sample was prepared at 10% (W/W) in methyl tert-butyl ether. The sample was mixed well. The standards and sample were run on an Agilent 6890 GC system with a flame ionization detector (Agilent Technologies, Santa Clara, California, USA) using a Phenomenex ZB-FFAP column (30 m, 0.32 mm ID, 0.5 um df; available from Phenomenex Inc., Torrance, California, USA).

Table 1 summarizes the residuals of monomers isooctyl acrylate, acrylamide, vinyl acetate, and 2,2'azobis-(2-methylbutyronitrile) initiator in three representative lots of base polymers.

TABLE 1

PPM Concentration of Residual Monomer and Initiator

| Sample | Isooctyl Acrylate | Acrylamide | Vinyl acetate | 2,2'azobis-(2-methylbutyronitrile) |
|---|---|---|---|---|
| 1 | <4 ppm* | <4 ppm* | 7.8% | 126 ppm |
| 2 | <4 ppm* | <4 ppm* | 6.4% | 263 ppm |
| 3 | <4 ppm* | <4 ppm* | 5.9% | 240 ppm |

*the level of detection by the method used is 4 ppm

Antimicrobial Testing—Direct Time Kill Test for Examples 1-4

The Direct Time Kill Test may be used to assess the in vitro reduction of aerobic microbial populations after exposure to a test material for a given amount of time. The time is either 15 minutes or 90 minutes in the present Examples 1-4. The test material is neutralized at the sampling time and the surviving microorganisms are enumerated. The Direct Time Kill test is based on ASTM E 2315-03 (Reapproved 2008). The detailed procedure is described below.

Sample Preparation

All benchtop, forceps, and dies used in the sample preparation are disinfected with 70% isopropyl alcohol and allowed to dry before use. On the disinfected benchtop, TRANSPORE tape, available from 3M Company, St. Paul, Minnesota, USA, is adhered to the backing side of each test material (not the removable release liner), with the first two layers of TRANSPORE removed from the roll before use to avoid contamination. Test materials consist of varying concentrations of formulations and octenidine dihydrochloride. Each material is tested in triplicate samples. A disinfected 1-inch diameter die is used to cut out 1-inch diameter samples of each test material. The same 1-inch die is used to cut out 1-inch diameter samples from 9965 Double Coated Tape (3M Company, St. Paul, Minnesota, USA). Using disinfected forceps, the 1-inch diameter samples and 9965 Tape are placed in sterile petri dishes.

Sterile forceps are used to remove the liner from one side of the 9965 tape, exposing the adhesive. The 9965 Tape adhesive side is adhered to a single microscope glass slide and placed in an individual sterile petri dish (1 slide with 9965 Tape per petri dish). The second liner on the opposite side of the 9965 Tape is removed, and the TRANSPORE tape side of the sample is adhered to the 9965 tape adhesive so that the release liner side of the sample faces up. The release liner is removed from the sample, exposing the test material adhesive before bacterial inoculation.

Testing Procedure

A bacterial suspension (about $10^7$ cfu/mL) is prepared from an 18-24 hour *Staphylococcus aureus* ATCC 6538 Trypticase Soy Agar culture plate using a 0.5 McFarland turbidity standard. Using a sterile 50 μL Combitip attached to an Eppendorf repeating pipettor (about 3 μL/droplet), place 15 droplets (about 45 μL) of the bacterial suspension across the test material adhesive of each sample. The petri dish cover is replaced and samples are incubated for 15 or 90 minutes in a 32° C. incubator.

After incubation, each sample (still adhered to the glass slide) is placed into 20 mL 2× concentration of DIFCO Neutralizing Buffer. The samples are sonicated for one minute and vortexed for two minutes. Enumeration of the test samples is performed by serial ten-fold dilutions in Butterfields Buffer. After dilution, 1 mL from each dilution is plated in duplicate with about 15 mL of molten trypticase soy agar (tempered at about 45° C.) poured and added into the plate. The plate is then swirled to ensure mixing of the trypticase soy agar and 1 mL sample and allowed to solidify before incubation at 35° C. for 24-48 hours. After incubation, plates are counted and recorded.

Calculations

The colony-forming units ("CFU") recovered from each sample are calculated using plates with counts from 30-300 CFU per plate. The CFU counts are then averaged between the sample duplicate plates and $\log_{10}$ transformed to achieve the $\log_{10}$ recovery per sample. The sample $\log_{10}$ reduction is calculated by subtracting the logic recovery of each sample from the average log recovery of the control or positive control samples (control/positive control n=3). The final average $\log_{10}$ reduction of each test material is achieved by averaging the triplicate sample log reductions.

Example 1

Adhesive Sample 1 Preparation: Base acrylate polymer (12.04 g, 28 wt. % solids) prepared as described above was added to a 4 oz. glass jar. To the jar was added glyceryl monoisostearate (1.2 g), triethyl citrate (0.22 g), 1-methoxy-2-propanol (4.56 g), ethyl acetate (0.33 g), methanol (1.63 g), and octenidine dihydrochloride (0.02 g). The glass jar was placed on a roller and rolled at 20 rpm for 12 hours at room temperature (about 23° C.). The adhesive solution was then coated (50 μm thickness) on a 2.5 mil silicone coated D 11 Green PRT paper release liner (Expera Specialty Solution, Kaukauna, Wisconsin, USA) and dried at 60-70° C. for 15-25 minutes to remove the solvent. The adhesive was laminated to PELLETHANE 5863-86A-VG film (20 μm thickness).

Adhesive Samples 2-6 and Comparative Example 1 ("CE-1") were prepared following the procedure described above for adhesive Sample 1 with solid ingredient amounts as listed in Table 2. The adhesive samples were used to carry out the Direct Time Kill Test (samples were incubated for 15 minutes) as described above. The 15-minute log reduction results for the various adhesive compositions are shown in Table 2.

TABLE 2

Adhesive Sample Formulations and Direct Time Kill Test Results

| Adhesive Sample | Octenidine Dihydro-chloride wt. % | Glyceryl Mono-isostearate wt. % | Triethyl Citrate wt. % | Base Polymer wt. % | 15-Minute Log Reduction |
|---|---|---|---|---|---|
| 1 | 0.5 | 25 | 4.5 | 70 | 5.09 |
| 2 | 0.5 | 22.5 | 7 | 70 | 5.50 |
| 3 | 0.5 | 20 | 9.5 | 70 | 5.58 |
| 4 | 0.5 | 28.5 | 4.5 | 66.5 | 5.48 |
| 5 | 0.5 | 27.75 | 7 | 64.75 | 4.54 |
| 6 | 0.5 | 27 | 9.5 | 63 | 5.54 |
| CE-1 | 0.5 | 29.5 | 0 | 70 | 0.52 |

As the data in Table 2 show, the adhesive samples with octenidine dihydrochloride and triethyl citrate, a cidatrope, have 4-5 logs greater reduction of *Staphylococcus aureus* ATCC 6538 at 15 minutes than the adhesive sample CE-1 prepared with octenidine dihydrochloride but without triethyl citrate. These data demonstrate the synergistic effect of a citropone and octenidine dihydrochloride in killing bacteria.

Adhesive Sample 7 Preparation: Base acrylate polymer (12.04 g, 28 wt. % solids) prepared as described above was added to a 4 oz. glass jar. To the jar was added glyceryl monoisostearate (1.2 g), PRISORINE (0.22 g), 1-methoxy-2-propanol (4.56 g), ethyl acetate (0.33 g), methanol (1.63 g), and octenidine dihydrochloride (0.02 g). The glass jar was placed on a roller and rolled at 20 rpm for 12 hours at room temperature (about 23 Cp. The adhesive solution was then coated (50 m thickness) on a 2.5 mil silicone coated D 11 Green PRT paper release liner (Expera Specialty Solution, Kaukauna, Wisconsin, USA) and dried at 60-70° C. for 15-25 minutes to remove the solvent. The adhesive was laminated to Pellethane 5863-86A-VG film (20 μm thickness).

Adhesive samples 7-14 and Comparative Example 2 ("CE-2") were prepared following the procedure described above for adhesive sample 7 but including various cidatropes and solid ingredient amounts as listed as listed in Table 3.

TABLE 3

Adhesive Sample Formulations

| Adhesive Sample | Octenidine Dihydro-chloride wt. % | Glyceryl Mono-isostearate wt. % | Cidatrope | Cidatrope wt. % | Base Polymer wt. % |
|---|---|---|---|---|---|
| 7 | 0.5 | 25 | PRISORINE | 4.5 | 70 |
| 8 | 0.5 | 29 | PRISORINE | 0.5 | 70 |
| CE-2 | 0.5 | 29.5 | — | 0 | 70 |
| 9 | 0.5 | 25 | ARLAMOL | 4.5 | 70 |
| 10 | 0.5 | 25 | Diisopropyl adipate | 4.5 | 70 |
| 11 | 0.5 | 25 | Dibutyl sebacate | 4.5 | 70 |
| 12 | 0.5 | 25 | Triethyl citrate | 4.5 | 70 |
| 13 | 0.5 | 25 | Tributyl citrate | 4.5 | 70 |
| 14 | 0.5 | 25 | Myristyl alcohol | 4.5 | 70 |

Adhesion to steel, MVTR, Tensile at Break, Ultimate Elongation at Break, and Fn10 Modulus Tests were carried out on dressings samples including the adhesive samples 7-14 and CE-2 and the results are shown in Table 4.

TABLE 4

Adhesion to Steel, MVTR, Tensile at Break, Ultimate Elongation at Break, and Fn10 Modulus Test Results

| Adhesive Sample | Adhesion to Steel gram/cm | Upright MVTR $g/m^2$ 24 hr | Inverted MVTR $g/m^2$ 24 hr | Tensile at Break Kg | Ultimate Elongation at Break % | Fn10 gram |
|---|---|---|---|---|---|---|
| 7 | 25.6 | 567.8 | 659.0 | 3.0 | 880.2 | 90 |
| 8 | 32.3 | 620.9 | 971.4 | 3.6 | 870.7 | 90 |
| CE-2 | 33.4 | 625.0 | 714.9 | 3.0 | 814.5 | 90 |
| 9 | 23.4 | 637.5 | 750.2 | 3.1 | 736.5 | 90 |
| 10 | 30.1 | 650.2 | 781.2 | 3.2 | 753.6 | 90 |
| 11 | 24.5 | 652.6 | 779.0 | 3.3 | 820.4 | 90 |
| 12 | 30.1 | 674.7 | 754.0 | 3.0 | 835.9 | 90 |
| 13 | 30.1 | 628.8 | 740.6 | 3.4 | 748.3 | 90 |
| 14 | 27.9 | 663.0 | 747.6 | 3.3 | 803.0 | 90 |

The data shown in Table 4 suggest that adding acid a cidatrope to an adhesive formulation has no significant impact on the results of Adhesion to Steel, MVTR, Tensile at Break, Ultimate Elongation at Break, and Fn10 Modulus Tests for dressing samples including such adhesives.

Adhesive samples 7-14 and Comparative Example 2 ("CE-2") were used to carry out the Direct Time Kill Test (samples were incubated for 15 minutes) described above.

The 15-minute log reduction results for the various adhesive compositions are shown in Table 5.

TABLE 5

| Direct Time Kill Test Results | | | |
|---|---|---|---|
| Adhesive Sample | Cidatrope | Cidatrope wt. % | 15-Minute Log Reduction |
| 7 | PRISORINE | 4.5 | 2.10 |
| 8 | PRISORINE | 0.5 | 1.10 |
| CE-2 | — | 0 | 1.06 |
| 9 | ARLAMOL | 4.5 | 2.87 |
| 10 | Diisopropyl adipate | 4.5 | 1.95 |
| 11 | Dibutyl sebacate | 4.5 | 2.58 |
| 12 | Triethyl citrate | 4.5 | 3.15 |
| 13 | Tributyl citrate | 4.5 | 2.51 |
| 14 | Myristyl alcohol | 4.5 | 1.99 |

The antimicrobial efficacy data shown in Table 5 suggest that adding a cidatrope to the adhesive formulation improves Log Reduction efficacy. The cidatrope concentration and cidatrope identity appear to influence Log Reduction efficacy as some cidatropes and higher cidatrope concentrations result in better direct kill of *Staphylococcus aureus.*

Example 3

Adhesive Sample 16 Preparation: Base acrylate polymer (18.06 g, 28 wt. % solids) prepared as described above was added to a 4 oz. glass jar. To the jar was added glyceryl monoisostearate (2.02 g), PRISORINE (0.13 g), 1-methoxy-2-propanol (6.84 g), ethyl acetate (0.49 g), methanol (2.44 g), and octenidine dihydrochloride (0.01 g). The glass jar was placed on a roller and rolled at 20 rpm for 12 hours at room temperature (about 23° C.). The adhesive solution was then coated (50 μm thickness) on a 2.5 mil silicone coated D 11 Green PRT paper release liner (Expera Specialty Solution, Kaukauna, Wisconsin, USA) and dried in an oven at 60-70° C. for 15-25 minutes to remove the solvent. The adhesive was laminated to PELLETHANE 5863-86A-VG film (20 μm thickness).

Adhesive Samples 15, 17, and 18 were prepared following the procedure described above for adhesive sample 16 with different concentrations of octenidine dihydrochloride but the same ratio of PRISORINE to octenidine dihydrochloride, as listed in Table 6. Adhesive Samples 15-18 were used to carry out the Direct Time Kill Test (samples were incubated for 15 minutes and 90 minutes) described above. The 15-minute log reduction results and 90-minute log reduction results for the various adhesive compositions are shown in Table 6.

TABLE 6

| Direct Time Kill Test Results | | | | |
|---|---|---|---|---|
| Adhesive Sample | Octenidine Dihydrochloride wt. % | PRISORINE wt. % | 15-Minute Log Reduction | 90-Minute Log reduction |
| 15 | 0 | 4.5 | 0 | — |
| 16 | 0.2 | 1.8 | 0.47 | 4.02 |
| 17 | 0.3 | 2.7 | 0.37 | 4.84 |
| 18 | 0.5 | 4.5 | 1.40 | 6.37 |

The data in Table 6 suggest that there is an octenidine dihydrochloride dose response, i.e., the higher the octenidine dihydrochloride concentration is the greater the bacteria kill is.

Example 4

Sample CE-5 Preparation: Base acrylate polymer (12.54 g, 28 wt. % solids) prepared as described above was added to a 4 oz. glass jar. To the jar was added glyceryl monoisostearate (1.25 g), triethyl citrate (0.25 g), 1-methoxy-2-propanol (4.50 g), and methanol (1.49 g). The glass jar was placed on a roller and rolled at 20 rpm for 12 hours at room temperature (about 23° C.). The adhesive solution was then coated (50 μm thickness) on a 2.5 mil silicone coated D 11 Green PRT paper release liner (Expera Specialty Solution, Kaukauna, Wisconsin, USA) and dried in an oven at 60-70° C. for 15-25 minutes to remove the solvent. The adhesive was laminated to PELLETHANE 5863-86A-VG film (20 μm thickness).

Adhesive Samples CE-3, CE-4, and CE-6-8 were prepared following the procedure described above for Sample CE-5 but including different cidatropes as listed in Table 7. None of the Adhesive Samples CE-3-8 include octenidine dihydrochloride. Adhesive Samples CE-3-8 were used to carry out the Direct Time Kill Test (samples were incubated for 15 minutes) described above, and the 15-minute log reduction for the various Samples are shown in Table 7.

TABLE 7

| Direct Time Kill Test Results | | | | | |
|---|---|---|---|---|---|
| Adhesive Sample | Glyceryl Mono-isostearate wt. % | Cidatrope | Cidatrope wt. % | Base Polymer wt. % | 15-Minute Log Reduction |
| CE-3 | 25 | Diispropyl adipate | 5 | 70 | 0.12 |
| CE-4 | 25 | Dibutyl sebacate | 5 | 70 | 0.00 |
| CE-5 | 25 | Triethyl citrate | 5 | 70 | 0.03 |
| CE-6 | 25 | Tributyl citrate | 5 | 70 | 0.01 |
| CE-7 | 25 | Myristyl alcohol | 5 | 70 | 0.02 |
| CE-8 | 25 | ARLAMOL | 4.5 | 70.5 | 0.04 |

The data in Table 7 show that the cidatropes have very low to no antimicrobial efficacy in the absence of octenidine dihydrochloride.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. An adhesive composition comprising:

40 wt. % to 90 wt. % resin system, wherein the resin system is a pressure-sensitive adhesive comprising a polymer prepared from:

70 wt. % to 95 wt. % of a first monomer, wherein the first monomer is a low Tg acrylate monomer selected from the group consisting of iso-octyl acrylate, 2-ethyl hexyl acrylate, 2-octyl acrylate, and butyl acrylate;

1 wt. % to 25 wt. % of a second monomer, wherein the second monomer is a polar, non-acidic monomer selected from the group consisting of acrylamide, N-vinyl pyrrolidone, and hydroxyl alkyl acrylate; and 0 wt. % to 20 wt. % vinyl acetate or butyl vinyl ether;

0 wt. % to 59.49 wt. % plasticizer, 0.01 wt. % to 10 wt. % octenidine salt, and 0.5 wt. % to 59.99 wt. % cidatrope, the cidatrope selected from a $C_8$-$C_{26}$ alcohol, a $C_8$-$C_{26}$ ether, a $C_8$-$C_{26}$ amide, a $C_8$-$C_{26}$ ester, or a combination thereof;

water in an amount less than 1 wt %; and $C_2$-$C_5$ alcohol in an amount less than 1 wt %, wherein wt % is based on the weight of the adhesive composition.

2. The adhesive composition of claim 1, wherein the first monomer is iso-octyl acrylate and the second monomer is acrylamide.

3. The adhesive composition of claim 1, wherein the polymer comprises vinyl acetate or butyl vinyl ether.

4. The adhesive composition of claim 1, wherein the modulus of the pressure sensitive adhesive is 10,000 to 200,000 Pa at 25° C.

5. The adhesive composition of claim 1, wherein the resin system is characterized by a modulus of 50,000 to 1,000,000 Pa at 25° C.

6. The adhesive composition of claim 1, wherein the plasticizer is selected from the group consisting of glyceryl monoisostearate, glyceryl monooleate, decagylcerol hexaoleate, decagylcerol decaoleate, acetyltributyl citrate, and combinations thereof.

7. The adhesive composition of claim 1, wherein the composition is a dried composition.

8. The adhesive composition of claim 1, wherein the cidatrope and the octenidine salt are present in a weight percentage ratio of cidatrope:octenidine salt of 0.1:1 to 3000:1.

9. The adhesive composition of claim 1, wherein the octenidine salt is selected from the group consisting of octenidine dihydrochloride, octenidine gluconate, octenidine sulfate, octenidine acetate, and combinations thereof.

10. The adhesive composition of claim 1, wherein the plasticizer is glyceryl monoisostearate and the cidatrope is triethyl citrate.

11. The adhesive composition of claim 1, wherein the cidatrope is a $C_8$-$C_{26}$ alcohol selected from the group consisting of 1-tetradecanol, hexadecanol, 16-methyl-1-heptadecanol, and combinations thereof.

12. The adhesive composition of claim 1, wherein the cidatrope is a $C_8$-$C_{26}$ ether that is a propoxylated $C_2$ to $C_{18}$ alcohol having a degree of propoxylation of 2 to 50 moles per mole of alcohol.

13. The adhesive composition of claim 1, wherein the cidatrope is a $C_8$-$C_{26}$ amide is-selected from the group consisting of a coconut fatty acid monoethanol amide, a coconut fatty acid methyl ethanolamide, an alkyl alkanolamide, and a combinations thereof.

14. The adhesive composition of claim 1, wherein the cidatrope is a $C_8$-$C_{26}$ ester is selected from the group consisting of diisopropyl adipate, dibutyl sebacate, triethyl citrate, tributyl citrate, octyldodecyl neopentanoate, laureth-2-acetate, isopropyl myristate, trioctyldodecyl citrate, myristyl myristate, cetyl acetate, and a combinations thereof.

15. An article comprising:

a substrate, and an adhesive composition according to claim 1, wherein the adhesive composition contacts at least a portion of a surface of the substrate.

16. The article according to claim 15, wherein the article is a medical article.

17. The article according to claim 16, wherein the medical article is a self-adhesive dressing, a surgical drape, or a medical tape.

* * * * *